United States Patent [19]

Kyle

[11] Patent Number: 5,376,540
[45] Date of Patent: Dec. 27, 1994

[54] TRIGLYCERIDE OILS LABELLED WITH $^{13}$C PREPARED BY CULTIVATION OF MICROORGANISMS

[75] Inventor: David J. Kyle, Catonsville, Md.

[73] Assignee: Martek Corporation, Columbia, Md.

[21] Appl. No.: 936,248

[22] Filed: Sep. 24, 1992

Related U.S. Application Data

[62] Division of Ser. No. 525,820, May 21, 1990, Pat. No. 5,164,308.

[51] Int. Cl.$^5$ .............................. C12P 7/64; C12P 7/62
[52] U.S. Cl. ..................................... 435/134; 435/135; 435/946; 424/2; 554/227
[58] Field of Search ................ 435/134, 135; 554/227; 424/2

[56] References Cited

U.S. PATENT DOCUMENTS 3,854,240  12/1974  Oldham et al. ........................ 47/1.4
4,485,173  11/1984  Gierhart .............................. 435/134

FOREIGN PATENT DOCUMENTS 62-146597   6/1987   Japan .
63-216489   9/1988   Japan .
63-273484  11/1988   Japan .
63-295527  12/1988   Japan .
02025447   1/1990   Japan .
2206881A    1/1989   United Kingdom .
8900606     1/1989   WIPO .

OTHER PUBLICATIONS

Biological Abstracts, vol. 81, No. 4, (Feb. 15, 1986) Eicke, "The Present State of Bleaching in the Refining Process . . ." pp. 355–359.
Radioisotopy vol. No. 2, (1975) M. Matucha, "Higher Fatty Acids in Chlor. Yulgaris (Pyrenoidosa): Content Individual Acids and Use . . ." pp. 205–214.
Proceedings-World Conference on "Emerging Technologies in the Fats and Oil Industry . . .", (1986) C. Ratledge, pp. 318–330.
Chem. Abstracts, vol. 95, No. 13 (1981), Butler et al., "Modification of the Carbon-14 . . ." p. 316 and abs. No. 111201X, 112(3), pp. 371–374.
Chem. Abstracts, vol. 87, No. 19 (1978), Watkins et al., "$^{13}$C-trioctanoin: a nonradioactive . . ." pp. 261–262 and abs. No. 148249e 90(3), pp. 422–430.
Gladue et al., "Production of Eicosapentaenoic acid . . ." Proceedings of Sessions Lectures . . . vol. II (JOCS) (1988).
Caspary, Clin. Gastroenterol., 7:351–374 (1978).
Einarsson, et al., "$^{14}$C–Triolein Breath Test as a Rapid and Convenient Screening Test for Fat Malabsorption", (1982).
Korsten, et al., J. Lab. Clinl. Med., 109:62–66 (1987).
Journal of the American Medical Assocation, 247:1926 (1982).
Watkins, et al., Gastroenterology, 82:911–7 (1982).
Clandinin, et al., Am. J. Clin. Nutr., 48:587–91 (1988).
Chen et al., "$^{13}$C-Labeled fatty acids from microalgae", *Developments In Industrial Microbiology*, vol. 31, pp. 257–264.
Heoksema et al., "An EPA-Containing Oil from Microalgae in Culture," *Health Effects of Fish and Fish Oils*, Chandra, ed., ARTS Biomedical Publishers, Newfoundland, 1989, pp. 337–347.

*Primary Examiner*—David M. Naff
*Assistant Examiner*—Michael V. Meller
*Attorney, Agent, or Firm*—Rothwell, Figg, Ernst & Kurz

[57] ABSTRACT

Labelled triglyceride oils are produced for use in diagnostic breath tests. The process involves the cultivation of microorganisms capable of producing the oils in an appropriately controlled environment wherein the microorganisms are feed $^{13}$C or $^{14}$C labeled carbon substrates to induce the microorganisms to produce the labeled oils. The preferred labelled carbon substrate is a substrate containing $^{13}$C. The oil produced is preferably enriched in oleic acid. The microorganisms can be induced to produce the oil by nitrogen depletion during cultivation.

12 Claims, No Drawings

1

TRIGLYCERIDE OILS LABELLED WITH $^{13}C$ PREPARED BY CULTIVATION OF MICROORGANISMS

This is a division of application Ser. No. 07/525,820, filed May 21, 1990, U.S. Pat. No. 5,164,308.

FIELD OF THE INVENTION

This invention relates to diagnostic breath tests, and, more particularly, to labeled compounds for use in such breath tests. In a preferred embodiment, this invention relates to the production and use of $^{13}C$-labeled algal oil in such tests. Such tests are especially useful in the indication of various pathologies associated with the malabsorption of fatty acids in the gastro-intestinal tract or problems associated with fatty acid metabolism in the liver or pancreas.

BACKGROUND OF THE INVENTION

The first tests for detecting pathologies or problems associated with the ingestion of fats involved the obtention of stool samples and the measurement of their fat content. This method had associated with it the problems of collecting and analyzing stools.

Partially in response to these problems, alternative techniques for detecting problems with the ingestion or metabolism of fats using isotope-labeled fats were developed, as disclosed by Caspary, *Clin. Gastroenterol* 7:351-374 (1978). In this type of test, carbon 14 labeled triolein is administered orally to patients and the amount of carbon 14 ($^{14}CO_2$) radioactivity in the breath is measured. The amount of radioactivity provides a means of diagnosing fat malabsorption. The rate of appearance of the labeled $CO_2$ in the breath can be used to indicate various pathologies associated with the malabsorption of the substrate. In other words, the rate of appearance will indicate GI tract dysfunction. Also, the rate can be used to detect problems associated with the metabolism of the substrate, for example, liver or pancreas disorders. Additionally, the complete absence of labeled $CO_2$ in the breath is indicative of metabolic problems. Concerns over the long term effects of the ingestion of radioactive substances have precluded this test from being used with children and with women of childbearing age.

Watkins, et al., *Gastroenterology* 82:911-7 (1982), disclosed the diagnosis and differentiation of fat malabsorption using $^{13}C$-labeled lipids in breath tests. In general, a $^{13}C$ breath test involves the ingestion by the patient of a labeled substrate, i.e. fatty acid, labeled with $^{13}C$, followed by monitoring the carbon dioxide ("$CO_2$") in the exhaled breath of the patient using isotope ratio mass spectrometer ("IRMS") for the appearance of the labeled carbon over a period of time. Normal metabolism produces a rapid appearance of $^{13}C$ in the exhaled carbon dioxide as the fatty acids are metabolized. Useful labeled lipids included trioctanoin, triolein and palmitic acid. Triolein has been found to be a preferred substrate.

Triolein is a chemically-synthesized oil comprised of three oleic acid moieties esterified to glycerol, forming a typical vegetable oil-like triglyceride. In the past, the oleic acid moieties have been labeled with either $^{14}C$ or $^{13}C$ at only the C1 position, in part due to the widespread belief that not all carbons along the fatty acid chain are oxidized equivalently. Also, organic labeling reactions are simpler when only C1 is labeled. Since carbons other than C1 in the fatty acid were thought not to be equivalent to C1 in the fatty acid oxidation pathway only C1 was labeled.

Commercially available $^{13}C$-labeled triolein is a chemically synthesized product, which heretofore has been quite costly to produce. Typically, the selling price is between $700—$1,000 per gram. Inasmuch as a dose of 3-4 grams of lipid or about 50 mg/kg body weight is required to perform a proper diagnostic breath test in adult males, the test is a very costly one to conduct.

Replacement of the radioactive carbon with its stable isotope and subsequent detection using an isotope ratio mass spectrometer has now made the breath test safe for any population of subjects. However, because of the prohibitive costs associated with chemically synthesizing labeled triolein, the test has not yet enjoyed widespread success.

Accordingly, it would be desirable to have a method of producing labeled compounds for use in diagnostic breath tests which significantly reduces the cost of such compounds.

It is a further object of this invention to provide a method for obtaining fatty acids and triglycerides with high levels of $^{13}C$-enrichment for use in diagnostic tests. Such compounds would increase the sensitivity of the test and further reduce the cost.

SUMMARY OF THE INVENTION

This invention relates to the production of oils containing labeled compounds for use in diagnostic breath tests. Microorganisms known to produce the desired compounds in an oil are cultivated in the presence of a labeled carbon substrate. The microorganisms are induced to produce the desired compounds, incorporating the labeled carbon therein, and are recovered. Additionally, the invention relates to compounds of high label enrichment which are useful in diagnostic breath tests.

DETAILED DESCRIPTION OF THE BEST MODE OF PRACTICING THE PRESENT INVENTION

The present invention relates to the biological production of labeled compounds for use in diagnostic breath tests.

In general, a microorganism known to produce a desired compound in an oil is cultivated under controlled conditions. The carbon source provided to the microorganism is carefully selected to provide labeled carbon as the substrate. The microorganism selected is one which can be induced to synthesize significant quantities of the oil containing the desired compound. After oil synthesis is essentially completed, the microorganisms are harvested and the labeled compounds can be recovered.

Diagnostic breath tests can be used to monitor the rate of appearance, or the non-appearance, of gases, such as labeled $CO_2$, in the breath exhalate which normally are produced as a result of metabolism. Fatty acid metabolism, which results in the rapid appearance of $CO_2$ as each carbon in the acid chain is metabolized, is particularly adapted to monitoring by such tests. The triolein test is well known and this disclosure will, for convenience, refer to triolein and its substituent oleic acid components throughout. However, it is to be appreciated that other fatty acids can be, and are, produced by the method of the present invention and used to produce compounds useful in diagnostic breath tests. For example, labeled palmitic and linoleic acids also can be produced by the present invention, as can oils containing mixtures of any of these compounds and oleic acid.

Any type of microorganism known to synthesize an oil containing oleic acid can be used in the present invention. Examples of such heterotrophic organisms include oleaginous yeasts, such as Candida, Lipomyces, and Rhodosporidium, and fungi, such as Mortierella or Mucor. These organisms require a fixed carbon source. The oleaginous yeast *Apotrichium curvataum*, two strains of which are available from the American Type Culture Collection in Rockville, Md., having Accession Nos. 20508 and 20509, is a preferred heterotroph.

Preferably, autotrophic microorganisms, such as species of Ankistrodesmus, Chlorella, Platymonus, Ourococcus, Neochloris, Monallanus, Nannochloris, and Nitzschia are used. Photosynthetic algae are preferred, and of these the genus Neochloris is especially preferred. Such organisms, being photosynthetic, can utilize carbon dioxide ($CO_2$) as the carbon source.

Strains or mutants which produce enhanced levels of oil or enhanced levels of oleic acid in the oil as compared to other strains of the same species are preferred. Such strains could be obtained by treatment with a mutagenic substance followed by selection, techniques known to those of skill in the art.

An especially preferable microorganism for use in the present invention is *Neochloris oleoabundans*. Techniques for obtaining *N. oleoabundans* from the ocean are known to those of skill in the art. Additionally, *N. oleoabundans* is commercially available from the University of Texas Culture Collection No. 1185. Throughout the remainder of this specification, unless otherwise noted, the disclosure will relate to the use of *N. oleoabundans*. This focus is for illustrative purposes only and it is to be recognized that other microorganisms that produce oleic acid containing oils can be used.

Either $^{14}C$- or $^{13}C$-labeled oleic acid containing oils can be produced by the method of this invention. Because of the previously described problems associated with the ingestion of radioactive compounds, however, it is preferable to produce $^{13}C$-labeled oleic acid containing oils. Accordingly, although it will be appreciated that either type of labeled compound can be produced by the present invention, the focus of this disclosure will be on $^{13}C$-labeled compounds.

It is preferable to cultivate the microorganism in a controlled environment where the carbon source can be strictly regulated. Such environments greatly reduce the chances of contamination by a non-labeled carbon source. Suitable controlled environments include photobioreactors and fermentors, generically referred to as "bioreactors." Photobioreactors are preferred. Especially preferred are photobioreactors such as those disclosed in U.S. patent application Ser. No. 440,084, filed Nov. 22, 1989, incorporated herein by reference. Other types of photobioreactors can also be used if desired. Autotrophs, such as *N. oleoabundans*, preferably are cultivated in photobioreactors. Heterotrophs preferably are cultivated in fermentors.

The bioreactor is provided with a nutrient solution capable of supplying essential nutrients to the selected organism. For *N. oleoabundans*, such a nutrient solution has been described in *J. Phycol*, 21:72-81 (1985), incorporated herein by reference. It is understood that modifications to the nutrient solutions are within the purview of those of skill in the art and that the solution can be tailored to the requirements of particular species.

The nutrient solution, hereafter referred to as the "medium," is placed in the bioreactor. Generally, the reactor is filled to 80-90% of capacity. Where labeled $CO_2$ is used as a carbon source (i.e. the photobioreactor) the pH is initially adjusted using potassium hydroxide (KOH) to an alkaline pH, typically in the range of about 9 to 11. The reactor is purged with $N_2$ and then labeled $CO_2$ is bubbled into the medium until the pH reaches about 7.8. The pH is monitored by a built-in pH electrode. At a pH of about 7.8 $^{13}C$-bicarbonate is present in the medium. Alternatively, $^{13}C$-bicarbonate can be added to the medium directly. If this latter alternative is chosen, approximately 2 grams of bicarbonate per liter of medium desirably are added. While the amount of labeled substrate can vary, the number of labeled carbons in the product generally corresponds directly with the amount of labeled substrate.

When heterotrophs are used, the labeled carbon substrate is preferably sterilized separately from the reactor containing the growth medium. Then, it is added to the sterilized growth medium. An inoculum of the selected microorganism is added. The inoculum has been grown in a $CO_2$ enriched atmosphere. An enrichment of 2% $CO_2$ is preferred although other enrichments can be used. The inoculant medium also contains an enriched level of nitrate compared to the nitrate level in the photobioreactor. Desirably, the photobioreactor medium contains less than about 5 mM nitrate.

Generally, about 1 liter of 0.5-5 grams of inoculum per liter of medium are added per 44 liter bioreactor. Preferably 1 liter of about 1 gram of inoculum per liter is added.

The reactor is closed and gas is bubbled through an inlet port into the medium using an air recirculating pump of a type known to those of skill in the art. When autotrophs are used, this gas preferably comprises $N_2$. When heterotrophs are used, the gas can comprise air.

If photosynthetic organisms are selected, they are exposed to sufficient quantities of light, of the quality required for photosynthesis, to enable photosynthesis to occur. If desired, constant illumination can be provided. Alternatively, a photoperiod of about 12-18 hours per day can be provided. Preferably, about 50-350 $\mu E/m^2/sec$ of continuous illumination are provided. As carbon is metabolized by the organisms, the pH of the medium will rise. Monitoring the pH indicates the amount of carbon consumed. When the pH reaches about 8.0, enough additional $^{13}CO_2$ is bubbled through the medium to return the pH to about 7.8.

Photosynthesis generates oxygen ($O_2$) which preferably is removed periodically, desirably when the pH reaches 8.0 (i.e., just before $CO_2$ addition). The system is opened by the use of solenoid valves and the $O_2$ removed in an exhaust stream. The exhaust stream is passed through a 2M KOH solution to trap any $^{13}CO_2$ that could have co-exhausted.

Typically, the process utilizing autotrophs yields from about 1.5 to about 1.8 grams of biomass per gram of carbon added.

Slightly different procedures are employed when the microorganisms to be cultivated are heterotrophic. The cultivation desirably is carried out in a fermentor. While similar nutrient solutions can be added to the fermentor, the carbon source must be fixed and the reactor can be directly loaded with the carbon substrate. Preferably, $^{13}C$-glucose is the carbon substrate, although other labeled fixed carbon sources can be used. $^{13}$C-glucose can be obtained from various commercial sources, including Merck, Sharpe and Dohme, Inc. The percentage of labeled carbons in the substrate can vary. For example, in glucose from about 6% to about 99% of the carbons can be labeled. The amount of glucose desirably added to the fermentor varies with the organism to be cultivated and can be determined by persons skilled in the art using routine experimentation. Heterotrophs produce $CO_2$ during respiration which can be recovered by passing the exhaust gas through a 2M KOH solution. Since the $CO_2$ produced from a $^{13}$C-glucose substrate will include $^{13}CO_2$, this recovery is desirable. For example, the recovered labeled $CO_2$ can be used in photobioreactors. Typical fermentation yields are from about 0.3 to about 0.5 grams of biomass per gram of glucose.

In general, after the organisms have been growing for about 7 days, they deplete the nitrate in the medium. When this occurs, lipid production is induced. Cultivation is continued for about 7 days after the induction of lipid production. The specific cultivation times will depend upon the type of organism and can be determined without undue experimentation by those of skill in the art. Oil droplets will be visible under a light microscope at approximately the time for harvesting.

when the biomass density reaches a selected level of dried biomass per liter of medium the cells are harvested. For autotrophs, this biomass density typically is about 2-4 grams of dry biomass per liter. For heterotrophs, it can be about 20–50 grams of dry biomass per liter of medium. Harvesting can occur by, for example, centrifugation.

Prior to extraction of the labeled product, the biomass can be dried. Any conventional method of drying can be used, such as vacuum tray or spray drying. However, freeze drying is preferred. The dried cells are broken by methods known to those of skill in the art, such as bead or roller milling, for a sufficient time to break the cells, typically about three days. Subsequent filtration will remove the beads and any remaining coarse materials. The cells need not be broken if super critical fluid (SCF) extraction processes are used. Such processes are known to those of skill in the art.

If desired, the cells can be broken while still wet, using cavitation, shearing or ultrasonic techniques. The resultant broken cell mass then is dried using the previously described techniques.

The dried and broken cells, i.e. the biomass, are extracted with a suitable solvent. SCF extraction using $CO_2$ is preferred, although extraction of the broken biomass with solvents at atmospheric pressure is acceptable. Of the latter, hexane is a preferred solvent. The amount of hexane can vary, but desirably is from about 400–600 ml per 100 g biomass. Extraction with hexane for about 2 days is followed by filtration as described above. Preferably, about 6 ml of hexane per gram of biomass are used. Additional centrifugation removes any remaining non-soluble materials. Repeated washings of the pellets with the solvent ensures the obtention of as much oil as possible. Typically, 3 washings are sufficient. The supernatants are combined and the solvent removed using suitable techniques, such as a rotary evaporator. The resultant product is a dark green crude oil. Typically, the crude oil contains significant amounts of contaminants, such as diglycerides, pigments and sterol esters. To remove such contaminants, the crude oil can be dissolved in a solvent and a sufficient amount of bleaching earth (Amer. Oil. Chem. Soc.) added to the solution. The mixture then is stirred for from about 4 to about 18 hours at room temperature (for convenience), filtered, and the solvent evaporated. This process can be repeated until a light yellow oil is obtained. The light yellow oil generally is significantly composed of triglycerides, preferably about 90%.

To purify the triglycerides from the oil, a suitable technology is silica gel chromatography. The oil is dry packed onto a silica gel. Preferably the ratio of oil to gel is 1:2. The silica gel can have a varying mesh but typically is from about 200–400. A silica gel column is prepared and wetted with a suitable solvent such as hexane prior to loading the oil. Successive elutions result in separation of the triglycerides from other materials. A preferred elution sequence is pure hexane, a 93:7 ratio of hexane:diethyl ether, an 88:12 ratio of hexane/diethyl ether and pure diethyl ether. It is contemplated that other solvents and/or ratios can be used.

Removal of the solvent results in a pure oil rich in oleic acid. Typically a yield of 30–40% of such oil based on the dry weight of the biomass can be achieved. A typical fatty acid profile of the oleic acid-rich oil is:

| C16:0 | C16:1 | C16:2 | C18:0 | C18:1 | C18:2 | C18:3 |
|---|---|---|---|---|---|---|
| 17% | 5% | 6% | 1% | 45% | 22% | 4% |

The oil can itself be used in a diagnostic breath test if desired.

This oil is randomly labeled, i.e., carbons other than $C_1$ will be labeled. However, equivalent dose responses are obtained when compared with commercially available $C_1$ labeled triolein. Additionally, this randomly labeled oil produces a higher label recovery from the dose, typically about 80% versus about 50% in triolein. The higher label recovery means that smaller doses can be utilized. Without wishing to be bound by theory, this effect is believed to be a result of using a mixed triglyceride containing oil rather than a synthetic 100% enriched oleic product such as triolein.

Alternatively, if desired, labeled triolein can be synthesized easily from the oleic acid-rich oil. The biomass is saponified in situ. Preferably a reflux using ethanol and KOH for from about 1–3 hours is used. 90 to 95% ethanol and 1–3N KOH are preferred. The reflux mixture is filtered, diluted with water (preferably a one-to-one dilution) and extracted with a solvent such as hexane to remove any non-saponifiable contaminants such as pigments or sterols. Acidification of the aqueous extract releases the fatty acids which then are extracted with a solvent such as hexane. The solvent then is removed by, for example, rotary evaporation.

Low temperature crystallization followed by urea adduction results in labeled oleic acid being purified to greater than 90% without difficulty. Preferably, the oil remaining from the evaporation is dissolved in acetone, typically about five volumes of acetone, and subjected to a low temperature for a time sufficient for crystallization to occur. Typically, overnight at about $-20°$ C. is sufficient. The crystals are removed and the liquor containing the fatty acids saved. After removal of the solvent from the liquor it can be diluted in another solvent such as methanol and very pure urea crystals added. A preferred ratio is 1 g fatty acid: 3 g urea per 10 ml methanol. The mixture is heated until the urea is solubilized and then permitted to cool such that recrystallization occurs. The crystals are removed and washed with urea saturated methanol. The addition of acidified water to the crystals followed by a solvent removes the oleic acid from the adducts. Preferably the water is at about pH 2.0 and the solvent is hexane. Removal of the hexane produces a fatty acid fraction which is about 90% oleic acid. The oleic acid can be reacted with glycerol according to conventional technologies to form triolein. Mono and diglycerides contaminants can be removed using silica gel chromatography as previously described.

One advantage of the present invention is that a perlabeled substrate can be produced. Having each carbon in the fatty acid labeled is desirable when the compound is used in a breath test as the increased labeling increases the sensitivity of the test. Moreover, the patient can ingest lesser amounts of the labeled compounds and still be sufficiently tested.

The prior art single-labeled compounds provide a label at the C1 of each fatty acid chain. The present labeled compounds can provide a labeled carbon at each, or any, position of the fatty acid chain. Thus, one aspect of the present invention includes compounds which are highly enriched with $^{13}C$ that are useful in diagnostic breath tests. "Highly enriched" is defined herein as from about 6% to about 100% labeled. Preferred compounds include perlabeled fatty acids. An especially preferred compound is perlabeled oleic acid. Even if the present compounds are not perlabeled, all the carbons, including C1, typically are randomly labeled. These compounds have been found to be equally useful in diagnostic breath tests. Having more than a single label per fatty acid increases the sensitivity of the test because it reduces the amount of the oil which must be administered to a patient to achieve comparable dose responses.

Another significant advantage of this invention is the use of a refined biologically-produced oil in the breath test. Generally such oils are enriched in oleic acid content to from about 6% to about 100%. Such oils are especially preferred because of the higher label recovery rates, as previously described. They also are preferred because the additional step of synthesizing triolein is not required.

Any of the compounds produced by the above described processes, or their equivalents, can be used in diagnostic breath tests. In such tests, fatty acid metabolism or absorption problems in a patient can be diagnosed by administering to the patient a labeled oil prepared by a process described herein and subsequently monitoring the patient's breath for the appearance of labeled $CO_2$. If the patient possesses normal fatty acid metabolism, labeled $CO_2$ will promptly appear in the breath.

The invention having been generally described above, specific non-limiting examples for illustrative purposes are set forth below.

EXAMPLES

EXAMPLE 1

Production of 6% enriched triglycerides

*Neochloris oleoabundans* (University of Texas Culture Collection No. 1185) was grown in a shake flask or Roux culture bottle (500-700 ml) under constant illumination 100 $\mu E/m^2/sec$ to about 0.5-2.0 g dry weight/liter. The culture medium was as disclosed in *J. Phycol.* 21:22-81 (1985). While growing, the culture was bubbled with air enriched with 2% $CO_2$. The temperature was maintained at 26° C. After 3-4 days the *N. oleoabundans* had reached a sufficient density to be used as an inoculant in a 44 liter production tank. The 44 liter production tank was prepared by adding a nutrient solution having only 5 mM nitrate and no sodium bicarbonate. The pH was adjusted to 10.5. Bubbled through this media was 6% $^{13}C$-enriched $CO_2$ until the pH reached 7.8. 600 ml of the Roux bottle culture then was added as an inoculant. Continuous illumination was provided at an intensity of 350 $\mu E/m^2/sec$. The culture was grown for 14 days and harvested by centrifugation. The biomass yield was about 150 g dry biomass or 3-4 g/l. The biomass was freeze dried and pulverized in a roller mill with 50 g of ceramic beads for 3 days. 500-600 ml of hexane was added and maceration continued in the roller mill for 2 additional days. The material was then filtered to remove the beads and centrifuged to remove fine, nonsoluble material. To ensure all oil was obtained, the pellets were washed 3 times with 200 ml of hexane and the hexane supernatants pooled. The hexane was removed by rotary evaporation. This resulted in a yield of about 60 g of a dark green oil. This oil was dissolved in 500 ml of hexane and 6 g of bleaching earth added. The solution was stirred from 4-18 hours at room temperature and filtered through a Buchner funnel with celite material. The hexane was evaporated. The bleaching process was repeated and a light yellow oil was obtained. Chromatographic analysis indicated this oil to be about 90% triglyceride. The triglycerides were purified using silica column chromatography. Thirty grams of oil were dry packed onto 60 g silica (230-400 mesh). This was loaded on a column containing 600 g of silica gel (230-400 mesh) wetted with 600 ml hexane. The material was eluted with 200 ml hexane, 500 ml hexane:diethyl ether (93:7), 1200 ml hexane:diethyl ether (88:12) and 600 ml pure diethyl ether. The 88:12 fraction contained pure triglyceride was The solvents were removed by rotary evaporation. To ensure complete removal, the purified triglyceride was heated under reduced pressure. A final yield was obtained of 40-50 g of pure triglycerides having the following fatty acid composition:

| C16:0 | C16:1 | C16:2 | C18:0 | C18:1 | C18:2 | C18:3 |
|---|---|---|---|---|---|---|
| 19% | 5% | 7% | 2% | 45% | 20% | 2% |

EXAMPLE 2

Production of 65% enriched triglycerides

The oil was produced and purified as in example 1 except for the following changes. The nutrient medium in the photobioreactor contained 3 mM nitrate and 25 mM $NaH^{12}CO_3$. As the pH increased $^{13}CO_2$ was supplied from a bottle containing 90% $^{13}C$ enriched $CO_2$. The biomass yield was 100 grams. The yield of crude oil was 43 grams and the final 65% enriched yield was 25 grams. The oleic acid-enriched oil had the following fatty acid composition:

| C16:0 | C16:1 | C16:2 | C18:0 | C18:1 | C18:2 | C18:3 |
|---|---|---|---|---|---|---|
| 16% | 3% | 4% | 4% | 51% | 17% | 5% |

EXAMPLE 3

Production of 6% enriched triolein

Biomass cultivated and dried as in example 1 is saponified in situ with 3N KOH in 95% ethanol (200 ml/50 g biomass) by refluxing for 1-3 hours. This mixture is filtered, diluted with one volume of water and extracted with one volume of hexane. This extraction removes non-saponifiable components. The aqueous extract is then acidified to pH 3.0 with HCl, freeing the fatty acids, which are extracted with hexane. Two washes of hexane are applied. The solvent is then evaporated. The fatty acids are dissolved in 5 volumes of acetone and stored overnight at −20° C. This permits crystallization to occur. The crystals are removed by filtration and the liquor saved as an enriched oleic acid fraction. The solvent again is evaporated. The enriched oleic acid fraction is diluted in methanol and high purity molecular biology grade urea added in a ratio of 1 g fatty acid: 3 g urea: 10 ml methanol. The mixture is heated, solubilizing the urea, and allowed to cool for at least four hours. As the mixture cools, urea-fatty acid adducts crystallize. These crystals are removed by filtration and are washed with urea saturated methanol to remove any adhering contaminants. 50 ml of acidified water (pH 2.0) is applied to the crystals, freeing the fatty acids which then are extracted with 500 ml of hexane. The hexane is evaporated, producing a fatty acid fraction enriched to greater than 90% with oleic acid. Triolein is produced by esterifying 3 equivalents of the 90% oleic acid with glycerol by known techniques. The triolein is purified as were the triglycerides in Example 1.

EXAMPLE 4

Production of 65% enriched triolein

65% $^{13}$C-enriched triolein is prepared as in Example 3 except the biomass for the saponification is prepared as in Example 2 and two rounds of low temperature crystallization and urea adduction are necessary to obtain 90% purity of the oleic acid.

We claim:

1. Triglyceride oils randomly labeled with $^{13}$C produced by the process comprising:
    (a) providing to microorganisms in a controlled environment a carbon substrate enriched in $^{13}$C,
    (b) cultivating said microorganisms,
    (c) inducing the microorganisms to produce an oil randomly labeled with $^{13}$C and
    (d) recovering said oil.

2. Labeled oil produced by the process of claim 1, wherein said recovery comprises:
    (a) saponifying said cells in situ,
    (b) filtering said saponified cells,
    (c) diluting said filtrate with water,
    (d) extracting said diluent with a solvent,
    (e) acidifying said extracted diluent, and
    (f) extracting said acidified diluent with a solvent.

3. Triglycerides in accordance with claim 1, wherein about 6% to about 100% of the carbons of the triglycerides are $^{13}$C.

4. Triglycerides in accordance with claim 1, wherein said triglycerides comprise from about 40% to about 100% oleic acid.

5. Triglyceride oil randomly labeled with $^{13}$C, wherein the $^{13}$C-enrichment is from about 6% to about 100% of carbons of the oil, said oil produced by a process comprising:
    (a) providing to microorganisms in a controlled environment a carbon substrate wherein from about 6% to about 100% of the carbons are $^{13}$C,
    (b) cultivating said microorganisms,
    (c) inducing the microorganisms to produce oil randomly labeled with from about 6% to about 100% $^{13}$C and
    (d) recovering said oil.

6. A labeled oil in accordance with claim 5, wherein said oil comprises from about 40% to about 60% oleic acid.

7. The oil of claim 6, wherein the microorganisms comprise autotrophic microorganisms.

8. The oil of claim 7, wherein the microorganisms comprise species of the genera Ankistrodesmus, Chlorella, Platymonus, Ourococcus, Neochloris, Monallantus, Nanochloris or Nitzschia.

9. The oil of claim 6, wherein the microorganisms comprise heterotrophic microorganisms.

10. The oil of claim 9, wherein the microorganisms comprise oleaginous yeasts or fungi.

11. Triglyceride oils randomly labeled with $^{13}$C produced by a process comprising:
    (a) providing *Neochloris oleoabundans* in a photobioreactor with $^{13}$C-enriched $CO_2$ as a carbon substrate,
    (b) cultivating said *Neochloris*,
    (c) inducing said *Neochloris* to synthesize triglyceride oils randomly labeled with $^{13}$C, and
    (d) recovering said triglyceride oils.

12. Randomly labeled triolein produced by a process comprising:
    (a) providing *Neochloris oleoabundans* in a photobioreactor with $^{13}$C-enriched $CO_2$ as a carbon substrate,
    (b) cultivating said *Neochloris*,
    (c) inducing said *Neochloris* to synthesize triglyceride oils comprising oleic, palmitic and linoleic acids, random carbons of which are $^{13}$C,
    (d) recovering said triglyceride oils and
    (e) synthesizing triolein from glycerol and said triglyceride oils.

* * * * *

UNITED STATES PATENT AND TRADEMARK OFFICE
CERTIFICATE OF CORRECTION

PATENT NO. : 5,376,540
DATED : December 27, 1994
INVENTOR(S) : David J. Kyle

It is certified that error appears in the above-indentified patent and that said Letters Patent is hereby corrected as shown below:

In the Abstract: Line 5, "feed" should be -- fed --;
Col. 3, line 18, "Monallanus" should be -- Monallantus --; Col. 8, line 36, after "triglyceride" insert a period; Col. 8, line 37, delete "was";
In the Claims: Col. 10, line 15 (claim 5), after "produce" insert -- said --.

Signed and Sealed this

Eleventh Day of April, 1995

Attest:

BRUCE LEHMAN

Attesting Officer      Commissioner of Patents and Trademarks